United States Patent
Minjeur et al.

(10) Patent No.: US 11,807,090 B2
(45) Date of Patent: Nov. 7, 2023

(54) MOTOR VEHICLE WITH COGNITIVE RESPONSE TEST SYSTEM FOR PREEMPTIVELY DETECTING POTENTIAL DRIVER IMPAIRMENT

(71) Applicant: GM GLOBAL TECHNOLOGY OPERATIONS LLC, Detroit, MI (US)

(72) Inventors: Patrick Minjeur, Sterling Heights, MI (US); David H. Clifford, Royal Oak, MI (US)

(73) Assignee: GM Global Technology Operations LLC, Detroit, MI (US)

(*) Notice: Subject to any disclaimer, the term of this patent is extended or adjusted under 35 U.S.C. 154(b) by 698 days.

(21) Appl. No.: 16/821,374

(22) Filed: Mar. 17, 2020

(65) Prior Publication Data
US 2021/0291650 A1 Sep. 23, 2021

(51) Int. Cl.
*B60K 28/06* (2006.01)
*B60R 11/04* (2006.01)
(Continued)

(52) U.S. Cl.
CPC ............ *B60K 28/063* (2013.01); *A61B 3/113* (2013.01); *A61B 3/14* (2013.01); *A61B 5/0002* (2013.01);
(Continued)

(58) Field of Classification Search
CPC ..... A61B 5/163; A61B 5/6893; A61B 5/7435; A61B 5/0002; A61B 5/4803; A61B 5/168; A61B 5/7475; A61B 5/162; A61B 5/741; A61B 5/4845; A61B 3/113; A61B 3/14; B60K 35/00; B60K 28/063; B60K 2370/1434; B60K 2370/119; B60K 2370/148; B60K 2370/171; B60K 2370/152; B61B 5/18; B60W 50/14; B60W 40/08; B60W 40/09; B60W 2050/146;
(Continued)

(56) References Cited

U.S. PATENT DOCUMENTS

| 2011/0304465 A1* | 12/2011 | Boult | ..................... B60K 28/06 340/576 |
| 2017/0188979 A1* | 7/2017 | Volpe | ..................... A61B 5/349 |

(Continued)

FOREIGN PATENT DOCUMENTS

| CN | 1934596 A | 3/2007 |
| CN | 105593640 A | 5/2016 |

*Primary Examiner* — Christopher E Leiby
(74) *Attorney, Agent, or Firm* — Quinn IP Law

(57) ABSTRACT

A test system for detecting impairment aboard a motor vehicle includes an electronic control unit (ECU) and sensors in communication therewith. The sensors are positioned within a vehicle interior, and include at least a touch screen and a microphone, and possibly an eye-tracking camera. In response to receiving a start request indicative of a requested start event of the motor vehicle, the ECU executes instructions to initiate a cognitive response test via the sensors. The ECU determines a test score of a driver during the test while the motor vehicle remains off, compares the test score to baseline scores to determine a passing or failing test result, and executes a control action aboard the motor vehicle in response to the passing or failing test result. The ECU may disable or immobilize the motor vehicle in response to the failing test result.

20 Claims, 4 Drawing Sheets

(51) Int. Cl.
    *A61B 5/18*       (2006.01)
    *A61B 5/16*       (2006.01)
    *A61B 5/00*       (2006.01)
    *A61B 3/113*      (2006.01)
    *A61B 3/14*       (2006.01)
    *B60K 35/00*     (2006.01)

(52) U.S. Cl.
    CPC ............... *A61B 5/162* (2013.01); *A61B 5/18* (2013.01); *A61B 5/4803* (2013.01); *A61B 5/6893* (2013.01); *A61B 5/741* (2013.01); *A61B 5/7435* (2013.01); *A61B 5/7475* (2013.01); *B60K 35/00* (2013.01); *B60R 11/04* (2013.01); *B60K 2370/119* (2019.05); *B60K 2370/148* (2019.05); *B60K 2370/1434* (2019.05); *B60K 2370/152* (2019.05); *B60K 2370/171* (2019.05)

(58) Field of Classification Search
    CPC ... B60W 2040/0863; B60W 2540/225; B60W 2540/21; B60R 11/04
    See application file for complete search history.

(56)               References Cited

U.S. PATENT DOCUMENTS

| | | | |
|---|---|---|---|
| 2020/0289042 A1* | 9/2020 | Patton | A61B 5/7282 |
| 2021/0197832 A1* | 7/2021 | Matsunami | B60K 28/06 |
| 2022/0156870 A1* | 5/2022 | Jiang | H04L 65/40 |

* cited by examiner

MOTOR VEHICLE WITH COGNITIVE RESPONSE TEST SYSTEM FOR PREEMPTIVELY DETECTING POTENTIAL DRIVER IMPAIRMENT

INTRODUCTION

The present disclosure generally relates to improved methods and associated hardware implementations for performing real-time onboard testing and detection of possible impairment of a prospective driver within a motor vehicle or another mobile platform. The computer-executed solutions as described herein seek to deter or prevent impaired driving using available onboard sensors, navigation or infotainment touch screens, controller area network (CAN) bus connectivity, and vehicle telemetry capabilities. As a result, the present approach is readily integrated into a motor vehicle without requiring installation of specialized test equipment.

Responsible operation of a motor vehicle requires an operator or driver to remain attentive to the roadway and dynamic or static obstacles such as other vehicles, pedestrians, road signs, and traffic lights. The driver must have the ability to closely concentrate on the driving task in different weather conditions, to correctly estimate distance and closing speed, and to quickly adjust to changing conditions in a well-coordinated manner. Operation of a motor vehicle therefore requires that the driver maintain unimpaired cognitive function, reflexes, and motor skills in order to accurately acquire, process, store, and retrieve information and respond accordingly.

Police and other law enforcement personnel have the requisite skill set for detecting possible alcohol-based driver impairment based on observed driving behavior, such as erratic steering, braking, or acceleration maneuvers or the inability to remain in a driving lane. Once a suspected impaired driver has been stopped, a police officer is also able to accurately discern the driver's present level of impairment using various blood or breath-based field sobriety tests. However, alcohol is not the sole culprit when it comes to impaired driving. For instance, prescription drugs can cause distinct physiological and behavioral changes that can impair a driver's cognitive function and motor skills in a manner that may be similar to or different from the well-established impaired behavior resulting from excess alcohol consumption.

When it comes to preempting impaired driving by repeat offenders that are nevertheless permitted to operate a motor vehicle, automakers and after-market suppliers are able to retrofit in-vehicle sobriety testing devices tied to a vehicle ignition system. For instance, a motor vehicle may be equipped with specialized breath sensors in communication with an onboard control system. When a prospective driver is seated in a vehicle interior, the driver may blow into a straw to direct the driver's breath over a set of chemical sensors. The sensors and associated algorithms are then used to estimate the driver's blood alcohol content (BAC). Other approaches measure compounds on the driver's skin to the same ends. However, devices of this type tend to require integration of the specialized sensors and other associated hardware into the motor vehicle, and are geared primarily to determining BAC to the exclusion of other controlled substances. Therefore, there remains a need for improved testing systems and methodologies for accurately and unobtrusively detecting potential driver impairment with an overarching goal of preempting motor vehicle operation whenever such impairment is detected.

SUMMARY

A system is disclosed herein for detecting possible driver impairment aboard a motor vehicle. The disclosed system is configured to test a cognitive response of a human driver to a battery of audio and/or visual tests. Each of the tests is performed using available onboard sensors as set forth herein, and thus the present testing approach is characterized by a lack of reliance on chemical detection sensors or other specialized chemical detection hardware. For instance, embodiments of the disclosed testing strategy utilize the available functionality of an onboard telematics system in conjunction with input/output capabilities of an onboard navigation or infotainment system, and thus foregoes the need for integration of additional physical components or retrofitted devices such as the above-noted breath analyzer.

The present approach also ensures optimal test accuracy and validity by creating a pre-impairment baseline score database, which is thereafter used as a reference for evaluating a given test score. Additionally, the present approach may include modeling impairment test validity over time by correlating test scores with demonstrated driving behavior of the type monitored using the above-noted onboard telematics system.

As will be appreciated by those of ordinary skill in the art, telematics data may be provided in a modern motor vehicle using a vehicle telematics unit (VTU). A VTU is capable of automatically monitoring the present state of health of individual vehicle components and subsystems, ranges and times of operation, etc. Such telematics data may be reported to the driver and/or to an offboard network, for instance to provide periodic state of health updates or maintenance reminders. Additionally, the VTU is integrated with the motor vehicle to enable the VTU to closely monitor driving speed and other driving behavior over time, including frequency and abruptness of braking, steering, and acceleration actions. Drivers may elect to report such telematics data to an insurer in order to receive insurance discounts for a demonstrated history of responsible driving habits. Likewise, drivers of fleet vehicles may be required to consent to the collection and reporting of such data collection as a condition of employment and/or to comply with a rental or lease agreement. The present testing strategy leverages these and other existing capabilities to a different end, i.e., to help correlate test scores gathered using the present method and onboard sensors with past-demonstrated driving behavior. This allows an onboard electronic control unit (ECU) to adapt its tests and test analysis over time, with the ultimate goal of optimizing overall test validity.

Various options are described herein for implementing the present testing strategy. For example, the disclosed test system may include a Cognitive Response Ignition Disabler (CRID) logic block in communication with a powertrain controller. The CRID logic block could automatically prevent or delay the starting of the motor vehicle in response to one or more failed cognitive tests, thereby immobilizing or disabling the motor vehicle for a period of time. The present approach may eliminate the need for integration of specialized breath-based or touch-based sensors of the types noted above in favor of validated psychological and/or physiological tests of the driver's response time and accuracy, each of which is presented to the driver within the vehicle interior as described herein.

Exemplary tests performable by the disclosed system may incorporate a reflex/motor skills test, a verbal response test, an eye-tracking test, and/or other suitable tests in order to derive test scores and generate passing or failing test results using such scores. If the driver does not pass a given cognitive test, the CRID logic block may be used to transmit a request to the powertrain controller to prevent the motor vehicle from starting or being placed in a drive or reverse gear, and/or the test may be repeated one or more times before such a preventative control action is taken.

Additionally, a driver having failed the disclosed test may be presented with various options via a touch screen. For example, the ECU may display phone numbers of nearest-available ride services such as taxi services or commercial ride providers, or the ECU may display local bus routes. Other options include displaying corresponding phone numbers of friends, family, or other trusted contacts. The driver may then select a suitable option from the touch screen. If the motor vehicle is equipped with hands-free calling options, selection of the suitable option may include automatically placing a telephone call or sending a text message to the selected contact using voice commands.

In an exemplary embodiment, a test system for detecting driver impairment aboard a motor vehicle includes sensors positioned within a vehicle interior, with the sensors including at least a touch screen and a microphone. An ECU is in communication with the touch screen and sensors, and is equipped with a processor and memory on which is recorded instructions for performing the present cognitive response test. The ECU is configured, in response to receiving a start request indicative of a requested start event of the motor vehicle, to execute the instructions and thereby initiate the cognitive response test via the sensors. The ECU determines test scores from the cognitive response test and compares the scores to a calibrated baseline to determine a passing or failing test result. The ECU then executes a suitable control action aboard the motor vehicle in response to the test result, e.g., by disabling or immobilizing the motor vehicle in response to a failing test result.

The motor vehicle the above-noted VTU, which is configured to monitor actual driving behavior. The ECU in such an embodiment may be configured to update the calibrated baseline performance using telematics data from the VTU, with the telematics data being descriptive of the monitored actual/past-demonstrated driving behavior, e.g., braking, acceleration, speed, and/or velocity.

The ECU may be programmed with the aforementioned CRID logic block, such that the ECU, using the CRID logic block, is able to prevent or delay starting of the motor vehicle in response to the failing test result.

The above-noted cognitive response test may include a reflexive motor skills test in which the ECU displays moving icons on the touch screen, and simultaneously detects touch events in which the driver respectively touches or fails to successfully touch the moving icons according to a prompted order or sequence.

The cognitive response test may also include a verbal recognition test in which the ECU audibly prompts the driver with one or more questions that are broadcast into the vehicle interior over a speaker, and detects a verbal response of the driver using the microphone.

In some embodiments, the sensors include an eye-tracking camera, with the cognitive response test including an eye-tracking test in which the ECU directs the driver to look at different areas of the touch screen and/or a moving icon displayed thereon, and thereafter tracks the driver's gaze via the eye-tracking camera as the driver attempts to follow the moving target. Such a test is roughly analogous to the horizontal gaze nystagmus or HGN test performed by law enforcement personnel as a field sobriety test. In an HGN test, a police officer evaluates the driver's eye movements as the driver attempts to follow a stimulus without moving his or her head. The office observes the smoothness of eye tracking for saccadic movement that may be indicative of intoxication.

The control action responsive to a failing test result may optionally include displaying alternative ride options via the touch screen.

Embodiments of the present system organize the calibrated baseline performance into statistical data clusters. The ECU in such an embodiment is configured to assign the driver to one of the data clusters as an assigned cluster, and to thereafter compare the test score to the assigned cluster to detect a threshold deviation indicative of a failing test result.

A method is also disclosed herein for detecting driver impairment aboard a motor vehicle having a vehicle interior. In a possible embodiment, the method includes receiving a start request indicative of a requested start event of the motor vehicle, and then determining, via an ECU, a performance of a driver of the motor vehicle to a battery of cognitive response tests performed using onboard sensors while the motor vehicle is in an off state. The sensors include at least a touch screen and a microphone. The method additionally includes comparing the determined performance to a calibrated baseline performance using the ECU to thereby determine a test score, and thereafter executing a control action aboard the motor vehicle, via the ECU, in response to the test score.

A motor vehicle is also disclosed herein having a body defining a vehicle interior, a set of road wheels connected to the body, and a test system for detecting driver impairment aboard the motor vehicle. In a disclosed embodiment, the motor vehicle includes a plurality of sensors positioned within the vehicle interior, including a touch screen, a microphone, and an eye-tracking camera. An ECU is in communication with the sensors, and has a processor configured to access a calibrated baseline performance database. The ECU also includes instructions for performing a cognitive response test. In response to receiving a start request indicative of a requested start event of the motor vehicle, the ECU executes the instructions and thereby initiates the cognitive response test using the sensors.

The cognitive test according to a disclosed embodiment includes a reflex or motor skills response time test using the touch screen in which the ECU is configured to display moving icons on the touch screen and simultaneously detect touch events in which the driver touches the moving icons. The test also includes a verbal recognition test performed using the microphone in which the ECU broadcasts one or more questions within the vehicle interior and detects a verbal response of the driver via the microphone. Additionally, an eye-tracking test is performed using the eye-tracking camera in which the ECU directs the driver to look at different areas of the touch screen while the ECU detects a response speed of the driver via the eye-tracking camera.

The ECU in this disclosed embodiment is configured to determine a test score of a driver of the motor vehicle during the cognitive response test while the motor vehicle is off, compare the test score to the calibrated baseline performance to detect a failing test result, and execute a control action aboard the motor vehicle in response to the failing test result, including temporarily disabling or immobilizing the motor vehicle.

The above summary is not intended to represent every embodiment or every aspect of the present disclosure. Rather, the foregoing summary merely provides an exemplification of some of the novel aspects and features set forth herein. The above features and advantages, and other features and advantages of the present disclosure, will be readily apparent from the following detailed description of representative embodiments and modes for carrying out the present disclosure when taken in connection with the accompanying drawings and the appended claims.

Figure 1:
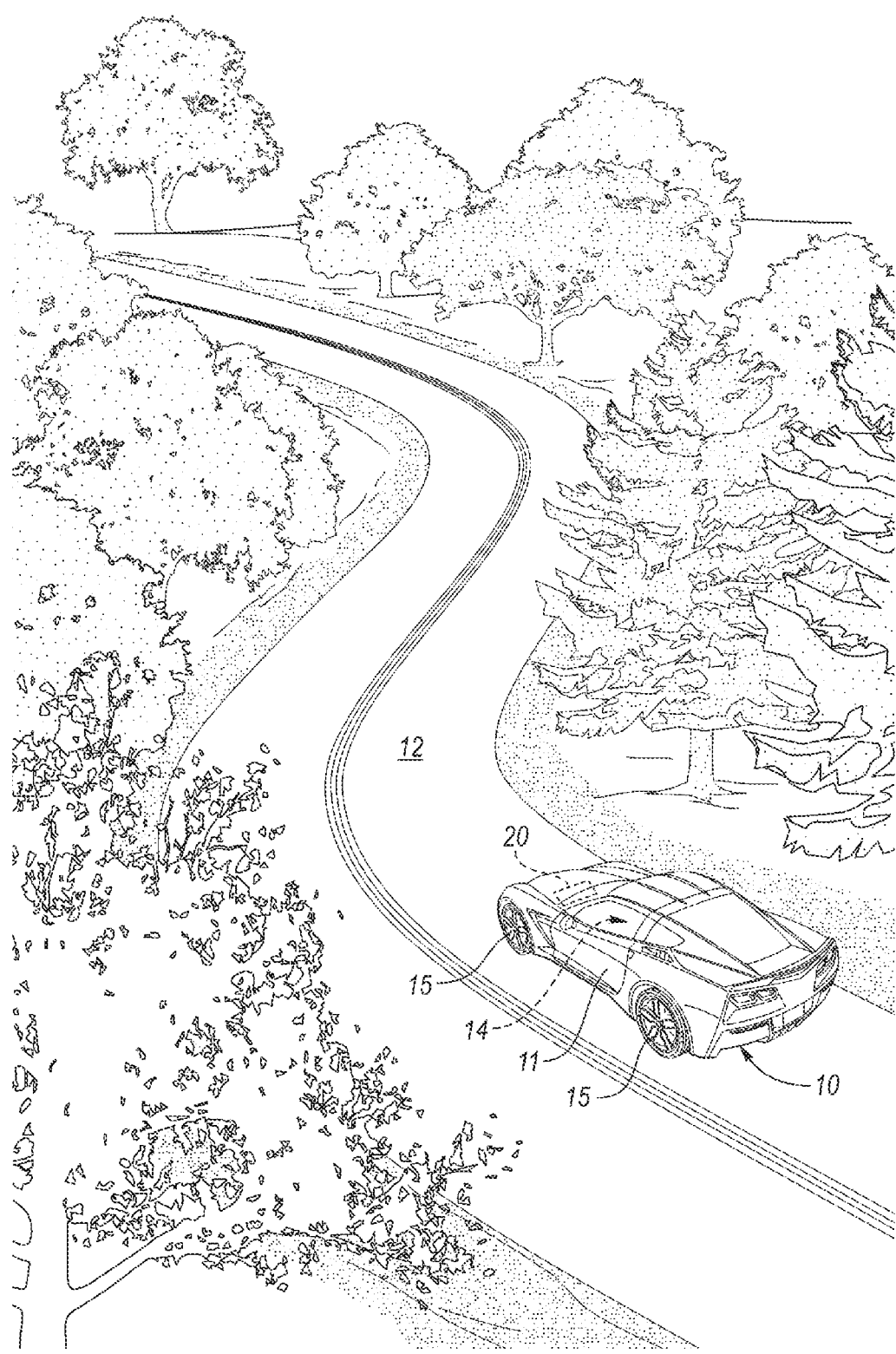
FIG. 1 is a schematic perspective view illustration of a motor vehicle equipped with a cognitive response testing system and associated testing control logic.

The present disclosure is susceptible to various modifications and alternative forms, and some representative embodiments have been shown by way of example in the drawings and will be described in detail herein. Novel aspects of this disclosure are not limited to the particular forms illustrated in the drawings. Rather, the disclosure is intended to cover modifications, equivalents, combinations, or alternatives falling within the spirit and scope of the disclosure as defined by the appended claims.

DETAILED DESCRIPTION

The following detailed description is merely exemplary in nature and is not intended to limit the application and uses. Embodiments of the present disclosure are described herein in terms of functional and/or logical block components and various processing steps. Such block components may be realized by a number of different hardware components each configured to perform the specified functions. In addition, those skilled in the art will appreciate that embodiments of the present disclosure may be practiced to advantage in conjunction with a number of systems, and that the systems described herein are merely exemplary embodiments of the present disclosure.

Referring to the drawings, wherein like reference numerals are used to identify like or identical components in the various views, FIG. 1 schematically depicts a motor vehicle 10 traveling along a roadway 12. The motor vehicle 10 includes a vehicle body 11 connected to a set of road wheels 15. Other driver-operated vehicles or mobile platforms may be envisioned within the scope of the disclosure which may or may not have road wheels 15, and thus the motor vehicle 10 is used herein as a non-limiting embodiment benefitting from the present teachings. That is, the solutions disclosed herein may help ensure the responsible operation of boats and other watercraft, trains, trolley cars, and other types of rail vehicles, aircraft, and snowmobiles and various other tracked vehicles.

Under ideal conditions, i.e., when a driver of the motor vehicle 10 of FIG. 1 is not impaired and operates the motor vehicle 10 at or below posted speed limits on dry pavement, in good lighting conditions, and with no opposing traffic, operation of the motor vehicle 10 is relatively routine. However, the ability of the same driver to operate the motor vehicle 10 becomes increasingly difficult when the driver is even moderately impaired. Thus, it would be advantageous to conduct a non-intrusive evaluation of the driver's present level of impairment as a condition for enabling start-up and subsequent operation of the motor vehicle 10.

Figure 2:
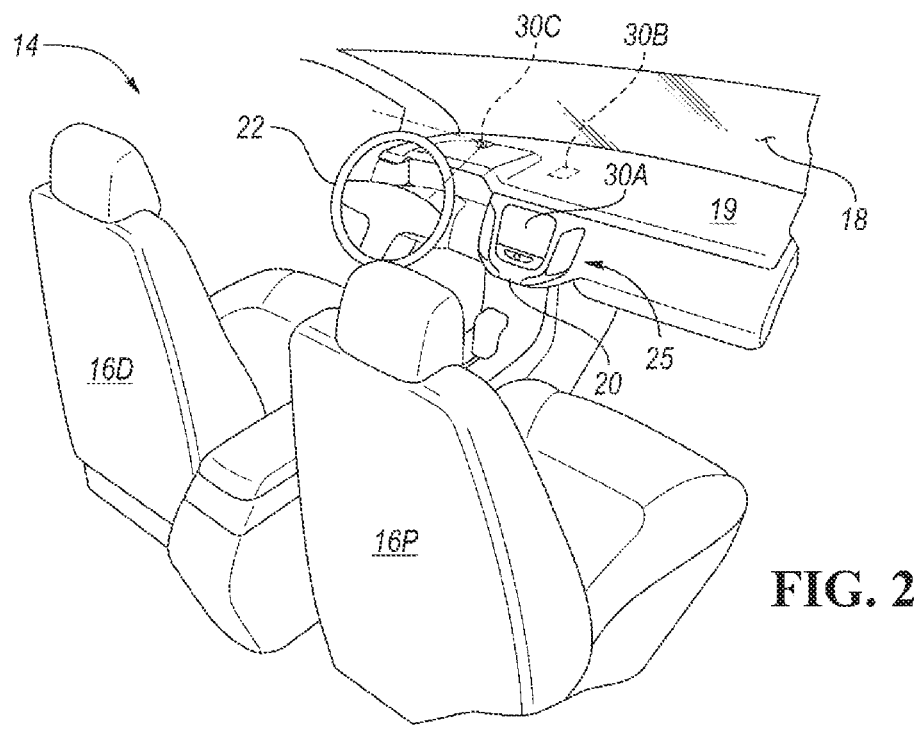
FIG. 2 is a schematic perspective view illustration of an exemplary vehicle interior having onboard sensors that are used to perform aspects of the cognitive response test disclosed herein.
Figure 3:
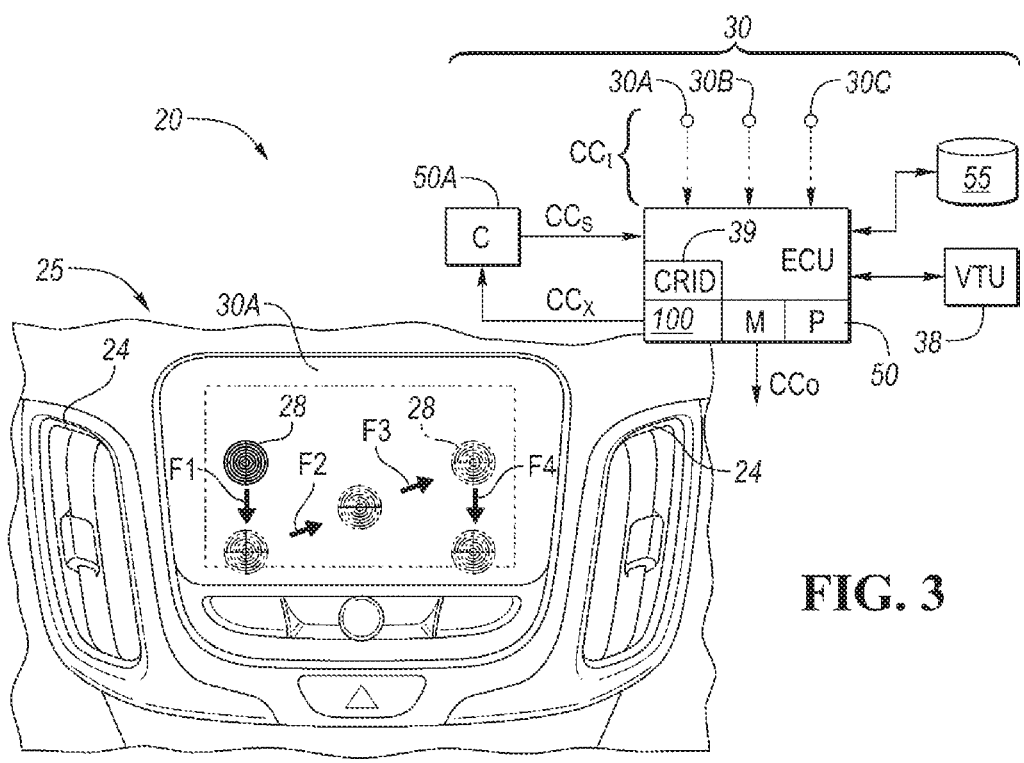
FIG. 3 is a schematic perspective view illustration of a vehicle center stack depicting a touch screen and representative testing control logic and associated hardware.
Figure 4:
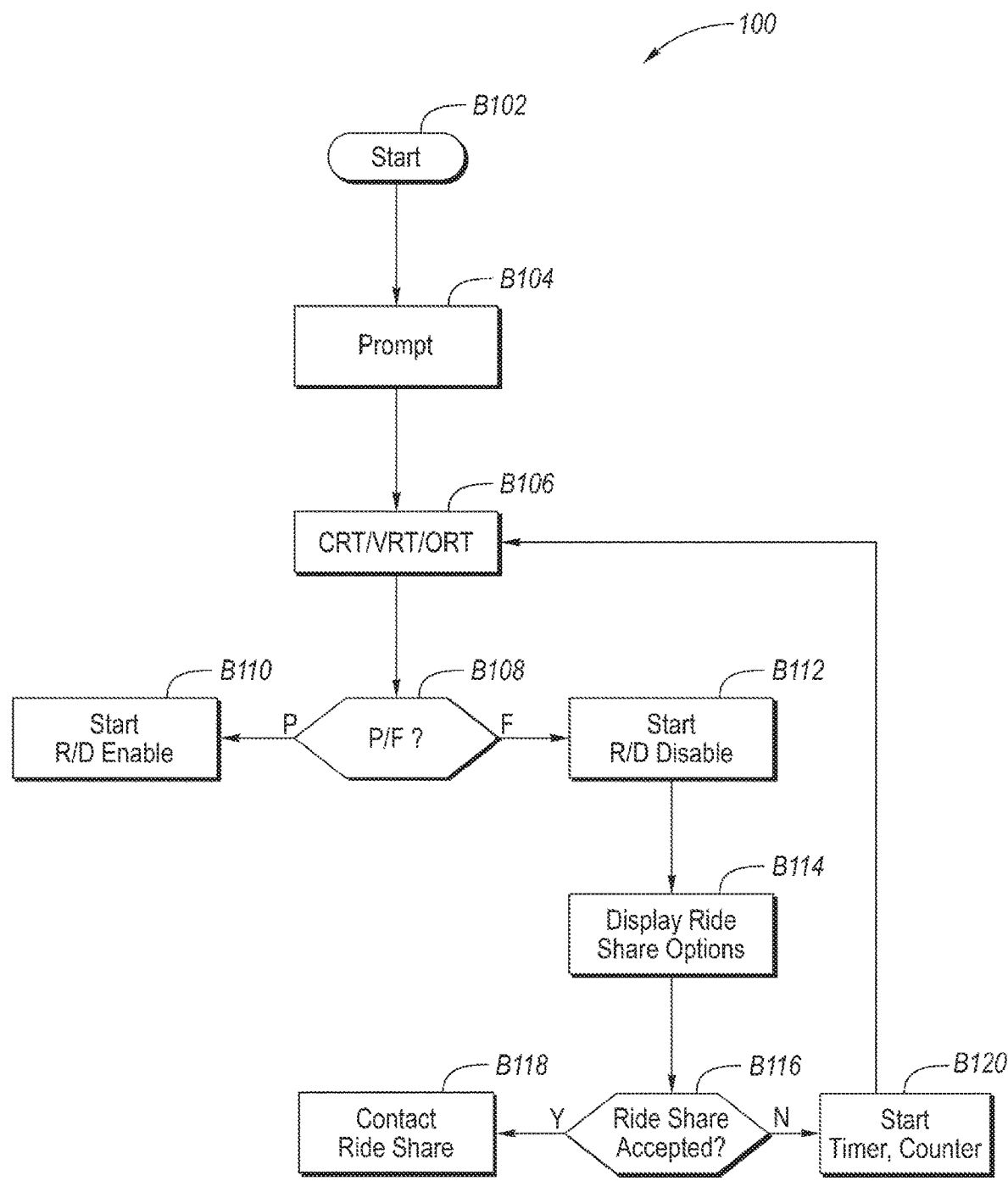
FIG. 4 is a flow chart describing a method that may be performed by the system shown in FIG. 3.

To that end, the motor vehicle 10 of FIG. 1 is equipped with a test system 20 constructed and operated as described below. Portions of the test system 20 are incorporated into a vehicle interior 14, i.e., a center stack 25 of the vehicle interior 14 as depicted in FIG. 2. Embodiments of the test system 20, such as but not limited to the representative embodiment of the test system 20 depicted in FIG. 3, are operable for detecting and quantifying a driver's responses to a predetermined battery of audio and/or visual tests, with the driver's collective responses thereafter scored. The test scores are compared to calibrated and adaptable baseline performance scores to detect possible impairment. An exemplary embodiment of a computer-executable method 100 for performing the present testing is shown in FIG. 4, with execution of instructions embodying the method 100 enabling the test system 20 to detect possible impairment and prevent operation of the motor vehicle 10 in response thereto.

Referring to FIG. 2, a non-limiting representative configuration of the vehicle interior 14 includes a driver seat 16D situated adjacent to a passenger seat 16P. In the illustrated configuration, a steering wheel 22 or other steering input device is positioned between the driver seat 16D and a windshield 18. Other possible configurations of the vehicle interior 14 are possible, including those in which the steering wheel 22 is located on the opposite side of the vehicle interior 14 and the positions of the driver seat 16D and passenger seat 16P are reversed.

Additionally as part of the vehicle interior 14 of FIG. 2, a dashboard 19 may extend from the windshield 18 toward the respective driver and passenger seats 16D and 16P as shown. The center stack 25 noted above may be situated between the respective driver and passenger seats 16D and 16P, and may be housed beneath the dashboard 19. The representative center stack 25 includes a touch screen 30A, e.g., of an infotainment system or navigation system. Such a touch screen 30A may be variously embodied as a capacitive, resistive, or optical touch-sensitive device and/or may include other suitable touch-sensitive technology in several optional non-limiting embodiments.

The test system 20 includes a plurality of sensors positioned within the vehicle interior 14 in proximity to the driver (not shown) when the driver seated in the driver seat 16D. While the term "driver" is used herein for simplicity, this term is intended to denote the position of a human occupant within the vehicle interior 14 as opposed to the status of such an occupant as an actual driver of the motor vehicle 10. That is, the driver is merely a prospective driver of the motor vehicle 10, and retains such a status unless and until operation of the motor vehicle 10 is enabled by successfully passing the cognitive impairment test described herein.

In a simplified exemplary embodiment, the sensors (collectively shown at 30 in FIG. 3) include at least the touch screen 30A and a microphone 30B, e.g., a BLUETOOTH-enabled microphone of the type used for hands-free communication with the infotainment system. While the microphone 30B is depicted on the dashboard 19 for illustrative clarity, the microphone 30B may be located anywhere within the vehicle interior 14, for instance integrated into a rear-view mirror or an overhead panel/control console, neither of which are visible from the perspective of FIG. 2. Additional sensors 30 may be used within the scope of the present disclosure, including but not limited to an eye-tracking camera 30C and associated tracking logic.

As will be appreciated, available examples of eye-tracking technologies operate in the optical or infrared range of the electromagnetic spectrum to detect a driver's eyes and thereafter track eye movement under various lighting conditions. Such an eye-tracking camera 30C may be used apart from the present method 100 as a tool for detecting and responding to distracted driving, and thus as an input sensor for a range of semi-autonomous driver assistance features. Likewise, the touch screen 30A and the microphone 30B may be used apart from the method 100 to facilitate infotainment, navigation, and telephony functions aboard the motor vehicle 10. Thus, the collective set of onboard sensors 30 enables the implementation of the present method 100 without resorting to installation of breath sensors or other special purpose testing sensors.

Referring to FIG. 3, portions of the test system 20 may be integrated into the center stack 25 as noted above. The touch screen 30A may be positioned between vents 24 of the center stack 25 in some embodiments, or at some other position that is comfortably reachable by the driver when seated in the driver seat 16D of FIG. 2. Additionally, an electronic control unit (ECU) 50 is in communication with the touch screen 30A, the microphone 30B, and the eye-tracking camera 30C. Collectively, the sensors 30 provide input data $CC_I$ to the ECU 50. In response to receipt of the input data $CC_I$, the ECU 50 executes the present cognitive response test to thereby detect possible driver impairment, with the ECU 50 possibly outputting control signals (arrow $CC_O$) to the various sensors 30 to implement the testing process. The ECU 50 does so using objective test results that are ultimately correlated with data stored in a calibrated baseline performance database 55.

The ECU 50, which is depicted schematically as a single control device in FIG. 3 for illustrative simplicity, may be alternatively implemented as a distributed network. The terms "ECU" and "control device" as used herein may be embodied as one or more application-specific integrated circuits or ASICs, electronic logic circuits, central processing units (CPUs), and/or microprocessors. The ECU 50 includes a processor (P) and memory (M) which together are configured to determine the driver's response to a battery of cognitive tests as set forth herein, and to thereafter access the calibrated baseline performance database 55 in determining the test scores and results. Instructions for performing the method 100 are recorded in the memory (M) and executed by the processor (P).

With respect to the memory (M), non-transitory memory components or storage devices may be used herein, including but not limited to read only memory (ROM), programmable read only memory (PROM), electrically-erasable programmable read-only memory (EEPROM), random access memory (RAM), etc. The non-transitory memory component is capable of storing machine readable instructions in the form of one or more software or firmware programs or routines, combinational logic circuit(s), input/output circuit(s) and devices, signal conditioning and buffer circuitry and other components that can be accessed by one or more processors to provide a described functionality.

Input/output circuit(s) and devices include analog/digital converters and related devices that monitor inputs from the sensors 30 as well as other possible sensors, with such inputs monitored at a preset sampling frequency or in response to a triggering event. Software, firmware, programs, instructions, control routines, code, algorithms and similar terms mean controller-executable instruction sets including calibrations and look-up tables. Communication between the ECU 50 and other controllers, including the additional controller (C) 50A described below, may be performed over a direct wired point-to-point link, networked communications bus links, differential voltage bus, wireless links, BLUETOOTH, and/or other suitable communication link(s), and using an associated communications protocol. Communication as contemplated herein includes the process of exchanging electronic data signals, electromagnetic signals, optical signals, and the like. The data signals may include discrete, analog, digital, or digitized analog signals representing inputs from the sensors 30, actuator commands, and communication between the ECU 50, the controller 50A, and possibly other controllers.

The motor vehicle 10 shown schematically in FIG. 1 may also include a vehicle telematics unit (VTU) 38 in communication with the ECU 50. As will be appreciated by those having ordinary skill in the art, telematics systems such as the schematically-depicted VTU 38 monitor ongoing driving behavior and component and subcomponent system status, with the ECU 50 of the present disclosure configured to periodically update a calibrated baseline performance of the driver using telematics data from the VTU 38 descriptive of the monitored driving behavior. For instance, the VTU 38 may provide the data during execution of a process 135 as described below with reference to FIG. 7.

As will be appreciated, telematics systems such as the representative VTU 38 are typically adapted for short-range wireless communication and/or cellular communication, and may be an OEM-installed (embedded) or aftermarket systems enabling wireless voice and/or data communication over a suitable carrier system. Such communication enables the motor vehicle 10 to communicate with a remote server, other telematics-enabled vehicles, or to communicate with another external entity or device. The VTU 38 likewise may employ radio transmissions to establish voice and/or data communications channels with a wireless carrier system so that voice and/or data transmissions are sent and received over the established channels. Data may be sent via data connections, such as packet data transmission over established data channels, or over voice channels. For combined services that involve both voice communication and data communication, the VTU 38 may utilize a single call over a voice channel and switch as needed between voice and data transmission over the voice channel, with such techniques being established and well understood in the general art.

Still referring to FIG. 3, the ECU 50 may be configured to receive a start request (arrow CCs) from the controller 50A, with the controller 50A possibly embodied as an engine control unit or a hybrid control unit. The start request (arrow CCs) may be an electronic signal indicative of a requested ignition or start event of the motor vehicle 10. In response to receipt of the start request (arrow CCs), the ECU 50 may selectively execute instructions embodying the method 100 so as to initiate the above-noted cognitive response testing processes. Such testing proceeds using the input data (arrows CO from the various sensors 30. To this end, the ECU 50 may be programmed with a Cognitive Response Ignition Disabler (CRID) logic block 39 such that the ECU 50, via the functionality provided by the CRID logic block 39, is able to prevent or delay a starting event of the motor vehicle 10.

Upon completion of a battery of cognitive response tests, the ECU 50 scores the driver's test performance, and may thereafter compare the test score to the calibrated baseline performance database 55 to thereby determine if the test score corresponds to a passing or failing test result. The ECU 50 thereafter executes a control action aboard the motor vehicle 10 in response to the test result. For instance, the ECU 50 may respond to a failing test result by communicating a start disable request (arrow CCx) to the controller 50A to thereby request that the motor vehicle 10 be immobilized or disabled as described below with reference to FIG. 4.

Cognitive Response Test

A cognitive response test as envisioned herein and automatically performed by the ECU 50 may include a test of the driver's present motor skills or hand-eye coordination. Reflex testing of this nature is performed using the display capabilities of the display screen 30A. For instance, the ECU 50 may command the display screen 30A to perform an animated video or other dynamic content that the driver is required to respond to via touch input to the touch screen 30A. A possible embodiment is that of a reflexive "tap-test" in which icons 28 forming moving targets are dynamically displayed via the touch screen 30A by operation of the ECU 50. As used herein, the term "icon" refers to a picture or a symbol, e.g., a "bullseye" target, circle, avatar, or other calibrated or user-selected/customizable image or animation.

In an exemplary embodiment, the ECU 50 may display and/or broadcast prompts asking the driver to sequentially tap the icons 28 as the icons 28 move around the touch screen 30A, with the driver doing so as quickly as possible. Such movement of the icons 28 is represented in FIG. 3 by arrows F1, F2, F3, and F4, with the icon 28 initially displayed in the upper left corner of the touch screen 30A. The icon 28 may remain at that position until touched by the driver, which then triggers the ECU 50 to move the icon 28 to another location, as indicated by arrow F2. The icon 28 may remain at the new position until touched, with the touch event then triggering the ECU 50 to move the icon 28 to new position as indicated by arrow F3. Likewise, a touch event of the relocated icon 28 results in the ECU 50 relocating the icon 28 yet again, as indicated by arrow F4. Other embodiments may not wait for the touch event, instead continuously or periodically relocating the icon 28 in a random manner and counting erroneous or delayed touch events.

While the above sequence is executed, the ECU 50 measures the physical response time and accuracy of the touch inputs, with the collected test performance data thereafter scored and used as part of the method 100 to determine the driver's present state of impairment. Other dynamic projections and/or video game-like animations may be used to similar effect, with the relocated positions of the icons 28 possibly varying in a randomized order to minimize test fatigue or to prevent a driver from being able to anticipate the next location of the relocated icon 28. Likewise, variation or optional customization of the icons 28 may help provide a more pleasing or interactive experience during repeated testing.

As part of the cognitive response test, the ECU 50 may employ speakers (not shown) arranged within the vehicle interior 14 of FIG. 2 to perform an audible recognition test. In such a test, the ECU 50 may be configured to verbally prompt the driver with one or more questions through activation of one or more of the speakers, and to detect the driver's spoken verbal response via the microphone 30B. For example, the ECU 50 may broadcast words, phrases, letters, and/or numbers, and may request that the driver, as quickly and accurately as possible, repeat the displayed information. As an audible test assumes the ability of the driver to comprehend the audible prompts, the ECU 50 may be configured to operate this phase of cognitive response testing in a driver-selected native language. When the driver's hearing is impaired, or as an alternative to using audible query-and-response testing, the ECU 50 may display the same or other inquiries via the display screen 30A, with the driver responding verbally to the various inquiries.

Similarly, the cognitive response test described herein may include use of the optional eye-tracking camera 30C when the motor vehicle 10 of FIG. 1 is so equipped. In this instance, the ECU 50 may direct the driver to progressively look at different parts of the touch screen 30A, possibly in conjunction with tracking of the above-noted icons 28 as the icons 28 are moved around the touch screen 30A. The eye-tracking camera 30C may thereafter record the driver's response time. The test performance during the described cognitive response test is then scored and compared online or offline to the calibrated baseline performance in the database 55 in order to compute a passing or failing test result and take appropriate control actions as needed.

FIG. 4 depicts a representative embodiment of the method 100, and is described with reference to the structure of FIGS. 1-3 as described above. The method 100 commences at block B102 with a requested start event ("Start") of the motor vehicle 10. Depending on the configuration of the motor vehicle 10, a requested start event may be performed by a driver having an unknown level of present impairment upon entering the motor vehicle 10 and pressing an ignition button or turning an ignition key. Remote start-equipped motor vehicles 10 equipped with the present testing logic may not start, or may start without enabling shifting of a connected transmission (not shown). Depending on the configuration of the test system 20, as part of block B102 the controller 50A of FIG. 3 may respond to an attempted start by transmitting the start request (arrow CCs) to the ECU 50. The method 100 then proceeds to block B104 in response to the start request.

Block B104 includes commencing cognitive response testing via the test system 20 described above, for instance by prompting ("Prompt") the driver with a message indicating that testing will soon commence. Such a prompt may be a display of text and/or broadcast of an audible message within the vehicle interior 14. The method 100 then proceeds to block B106.

At block B106, the ECU 50 proceeds with a battery of tests to evaluate the driver's present level of cognitive impairment. The ECU 50 may be configured to perform the same battery of tests in certain embodiments, such as the above-described cognitive response test (CRT)/tap-test and the audible/verbal response test (VRT). When the motor vehicle 10 is equipped with the eye-tracking camera 30C, tracking data supplied from the eye-tracking camera 30C may be used as part of an optical response test (ORT). Some embodiments of the method 100 may randomize the order of performance and/or the particular test or tests being performed. Or, the ECU 50 may perform the various tests in a progressively escalating manner, for instance by performing the audible test when the results of the reflexive tap test are borderline failing, or performing the optical response test/eye-tracking test when the results of the tap test and audible test are borderline failing. The method 100 then proceeds to block B108 after scoring the response accuracy for each of the tests, e.g., as a percentage or a raw score.

Block B108 includes determining, via the ECU 50 using the test results from block B106 in conjunction with the baseline data from the baseline performance database 55 of FIG. 3, whether the present test scores correspond to passing or failing test results, as abbreviated "P/F?" in FIG. 4. Possible construction and adaptation of the baseline data is described below with reference to FIGS. 5-7. The ECU 50 proceeds to block B110 in response to a passing (P) test result, with the ECU 50 proceeding in the alternative to block B112 in response to a failing (F) test result.

At block B110, the ECU 50 executes a suitable control action in response to the passing result at block B108. A suitable control action undertaken at block B110 may entail enabling the start of the motor vehicle 10 of FIG. 1 via communication with the responsible controller 50A, and subsequently enabling a reverse or drive shift (Start and R/D Enable). The method 100 is complete, and may resume anew with the next requested start of the motor vehicle 10.

At block B112, the ECU 50 executes a suitable control action in response to the failing result at block B108. A suitable failing control action may entail temporarily disabling start of the motor vehicle 10 of FIG. 1 via communication with the responsible controller 50A, as well as disabling a reverse or drive shift (Start and R/D Disable). The method 100 may thereafter proceed to block B114.

Block B114 is executed in response to a failing test result after the ECU 50 performs the control actions set forth in block B112. In an exemplary embodiment, the ECU 50 may display alternative ride options via the touch screen, e.g., by prompting the user with ride share options ("Display Ride Share Options") via the display screen 30A of FIGS. 2 and 3. Within the scope of the disclosure, ride sharing may encompass commercial, private, or municipal options such as but not limited to UBER and LYFT, or taxi, bus, shuttle, or other available transmit services. Options for block B114 also or alternatively include programmed telephone numbers of trusted friends or relatives, or any other individual or service providing a viable ride alternative. The method 100 then proceeds to block B116.

Block B116 includes determining, via the ECU 50, whether the driver has responded to the displayed ride sharing prompts by selecting a displayed option, whether via touch input to the display screen or using voice commands. The method 100 proceeds to block B118 when the driver has affirmatively selected a displayed ride share option. In the event the driver fails to select a displayed ride share option in an allotted time, e.g., within 10-20 s of the prompt being displayed on the touch screen 30A, the method 100 proceeds to block B120.

At block B118, the ECU 50 may automatically contact the selected ride share option, such as by activating hands-free calling functions of an onboard infotainment system housed in the center stack 25 of FIGS. 2 and 3. The method 100 is complete once the ride sharing option has been contacted. In the event block B118 is implemented as an automated display of a ride sharing application/app, aspects of block B118 may entail actions of the driver, with block B118 finishing with the display or activation of the app. Other implementations may include placing a hands-free phone call to the selected ride option or preparing a voice-to-text message via the ECU 50, as well as transmitting a pre-recorded default message as a text or voice message to the selected option. GPS coordinates and time of call may be appended to the transmitted message to facilitate location of the motor vehicle 10 and its driver.

At block B120, the ECU 50 may reference the current value of an integer counter and, if the counter value is less than a predetermined threshold number of allowed test iterations, e.g., 3-5, the ECU 50 may initiate an optional stopwatch timer ("Start Timer, Counter"). The timer may commence with failure of the driver to select a displayed ride option at block B116. Once the timer has reached a calibrated or preset time, e.g., 5-10 minutes, the ECU 50 may increment the above-noted integer counter and return to block B106, whereupon the method 100 continues with another testing iteration.

When the ECU 50 determines that the allowed number of test iterations has been reached, the ECU 50 may initiate not proceed beyond block B120. In such an instance, the ECU 50 may maintain the motor vehicle 10 in the disabled state implemented in block B112 for a more extended duration, e.g., several hours or more, such that the motor vehicle 10 is immobilized and not drivable until sufficient time has elapsed or the lock-out is overridden by an unimpaired secondary driver of the motor vehicle 10. Such an override option would allow a trusted contact to operate the motor vehicle 10 with the impaired driver now relegated to passenger status.

Figure 5:
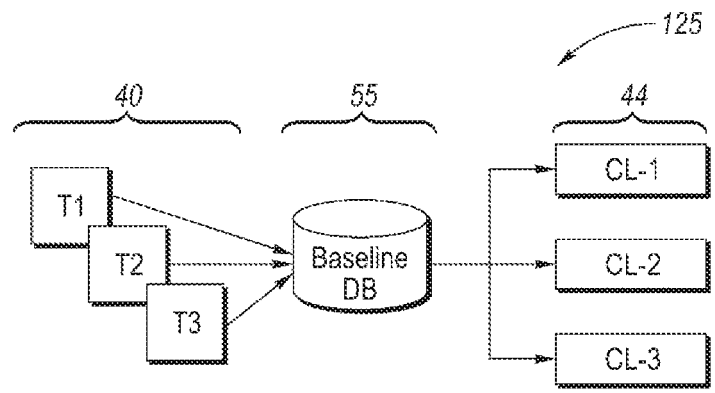
FIGS. 5-7 are schematic flow diagrams respectively describing construction of a pre-impairment baseline, a driver impairment assessment, and a test result validity baseline.

Referring to FIG. 5, effective implementation of the present method 100 is dependent upon construction of the pre-impairment baseline database 55. That is, in order for impairment testing to provide reliable, accurate, and repeatable results, the ECU 50 is first configured with data descriptive of reference/unimpaired test performance data.

As part of a pre-impairment baseline construction process 125, a number of discrete tests 40, labeled T1, T2, and T3 for simplicity, may be run on a sample population of unimpaired drivers. Tests 40 in some embodiments may be of the driver alone, e.g., by prepopulating the baseline database (Baseline DB) 55. Such a database 55 may be recorded in memory (M) and/or accessible thereby. Such tests could be performed at different times of day and/or on different days to assess the operator's unimpaired response times under a range of different conditions. In other embodiments, the tests 40 may be of a large population of drivers in a given geographic area or worldwide.

Once the database 55 has been populated with a sufficient amount of data to form a suitable reference level, the data may be separated by the ECU 50 or offline into a plurality of statistical data clusters 44, e.g., CL-1, CL-2, and CL-3. The ECU 50 may be configured to assign the driver to one of the data clusters 44 as an assigned performance cluster, and to thereafter compare the determined test performance to the assigned performance cluster to detect a threshold deviation or variance therefrom. As will be appreciated by those of ordinary skill in the art, cluster analysis is a statistical practice in which sampled data is classified into different groups, with similarly-classified data having maximal similarity falling into a given cluster. That is, a data performance cluster 44 separates different drivers into groups of similar characteristics. For instance, three different test types performed, such as the above-described response time, audible recognition, and eye-tracking test, could consistently produce high scores, or a low score on one of the three tests, or three different scores, with the various possibilities corresponding to a verified unimpaired driver.

Thus, the performance for the three exemplary test types describe herein could be plotted on a three-axis grid with each axis corresponding to one of the three tests. Drivers could be assigned to a given data cluster 44 that is normal/unimpaired for that particular driver. A driver could possibly be assigned to a particular data cluster 44 based on factors such as age, sex, visual and/or hearing acuity levels, prescription drug use, or other suitable factors. By way of example, such an approach would help ensure that the collective test performance of one group of similar drivers is not necessarily used as the pass/fail standard when evaluating the test performance of a group of dissimilar drivers. For instance, hand-eye coordination and hearing may degrade with factors such as age, past or present illness or disease, or temporary or permanent disability. In spite of such degradation, however, similarly situated drivers having the same or similar characteristics will exhibit a baseline unimpaired test performance. For improved test accuracy, therefore, the ECU 50 may separate drivers into a relevant data cluster 44, and restricting analysis of a given driver's test performance to the baseline for the driver's particular assigned data cluster 44.

When implementing the present testing, the ECU 50 is therefore able to compare the driver to a relevant set of baseline data in which unimpaired baseline levels are indicative of levels for the particular driver. Use of statistical data clustering may not be necessary in embodiments in which the database 55 is populated solely with data derived from tests of the driver alone. The driver's test results in such an embodiment would be compared to the driver's own unimpaired baseline results. Likewise, using an app or a website, optional embodiments may be considered in which the driver is able to perform impairment testing offline without entering the motor vehicle 10.

Figure 6:
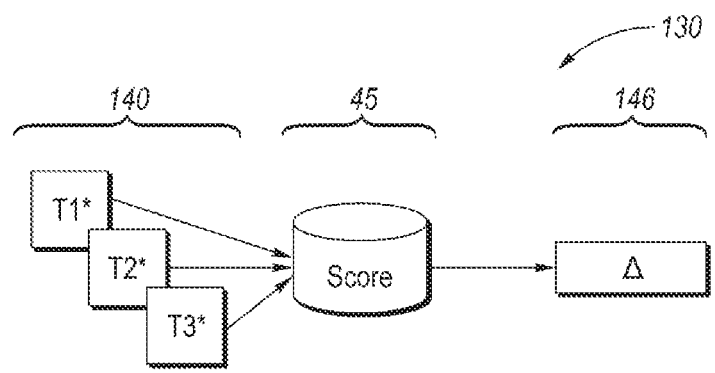

Referring to FIG. 6, an impairment assessment process 130 may be performed as part of the method 100 using impairment tests 140, labeled T1*, T2*, and T3* for simplicity. Unlike the baseline process 125 of FIG. 5, the tests 140 are performed during actual attempted starting events of the motor vehicle 10. The ECU 50 may receive the tests 140, score the tests 140, and record the results in a scoring database (Score) 45. The scores in the scoring database 45 may then be compared by the ECU 50 at a variance calculation block 146 to data in the baseline performance database 55 of FIG. 5 and an observed cluster-specific test performance to determine a score variance ($\Delta$), i.e., a score delta. The ECU 50 may then determine a passing or failing result at block B108 of FIG. 4 by comparing the score variance to a calibrated allowance variance or delta value.

Figure 7:
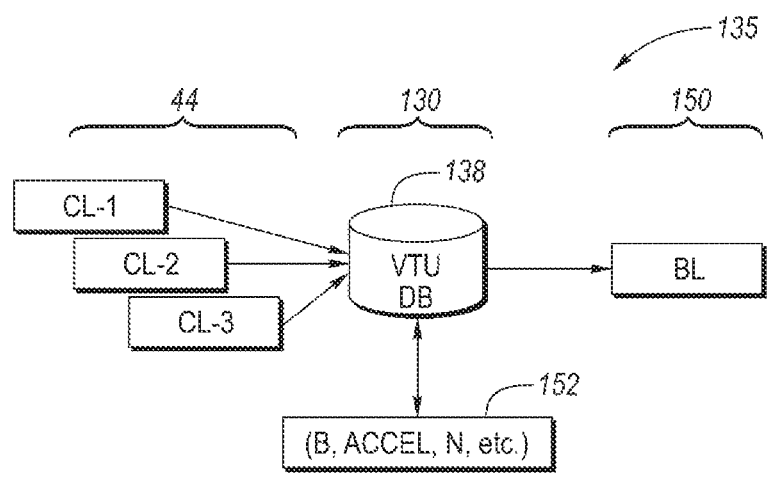

FIG. 7 depicts a process 135 for constructing a cognitive validity baseline over time, which enables the ECU 50 to adapt to updated data and, ultimately, to improve the testing accuracy of the impairment testing described herein. In general, the process 135 enables the ECU 50 to compare a given test score to the driver's demonstrated driving ability. For instance, the data clusters 44 shown in FIG. 5 may be correlated with telematics data collected via VTU data block 152. Such telematics data may include, by way of example, a braking history (B), acceleration history (ACCEL), and/or vehicle speed/trajectory (N), as well as steering history (not shown) and other possible driving behavior or history. As used herein, "history" refers to demonstrated hard or unwarranted harsh driving behavior relative to a given vehicle input device. As will be appreciated, a driver that consistently applies the brakes with excessive force, oversteers the motor vehicle 10, or rapidly accelerates may be doing so in order to compensate for impaired motor skills, reflexes, or cognition. Or, the same driver may simply be disposed toward such actions even when unimpaired.

Additionally, a particular driver may perform better on one battery of cognitive tests than another. Or, the driver may perform better on one test type, e.g., the reflexive "tap test", but due to reduced hearing acuity may not do quite as well on the audible recognition test. Likewise, a driver with sufficient visual acuity to legally operate the motor vehicle 10 may nevertheless have less than perfect vision. As a result of this or a myriad of other issues, the driver may not do as well on the eye-tracking test relative to the audible recognition or physical response tests. Thus, a telemetry database 138 may be used to track and record demonstrated driving behavior over time from provided vehicle telemetry data from the VTU 38 of FIG. 3, correlate the demonstrated driving behavior with a given data cluster 44 of FIG. 5, and adapt the baseline database 55 over time to improve test accuracy and ensure test validity.

Likewise, the process 135 shown in FIG. 7 may be used to evaluate relative driver impairment severity based on actual behavioral outcomes. For example, a driver receiving a borderline passing test result at block B108 of FIG. 4 may thereafter exhibit driving behavior indicative of possible impairment. Thus, the ECU 50 may use demonstrated driving behavior to correlate and validate test results at block B108, with such driving behavior possibly collected and reported by the vehicle telemetry database 138 upon driver opt-in, e.g., for insurance rate reduction, lease or rental contract, or for other purposes.

The method 100 of FIG. 4 when used in conjunction with the supplemental processes of FIGS. 5-7 therefore provides an improved in-vehicle testing strategy for evaluating a prospective driver for possible behavioral and physiological impairment. The present approach replaces the need for retrofitting the motor vehicle 10 with specialized hardware to prevent impaired driving, such as chemical detection devices or breath analyzers, with the present approach instead taking advantage of onboard infotainment systems, CAN connectivity, and possible wireless telemetry capabilities of the VTU 38 to enable non-intrusive in-vehicle testing, with logic of the method 100 possibly integrated in logic driving the center stack. Use of the method 100 thus provides ready assessment of cognitive response time while enabling real-time evaluation of associated driving behavior, with the ECU 50 adapting test scoring and passing/failing reference scores over time to help ensure test validity. These and other benefits will be readily appreciated by one of ordinary sill in the art in view of this disclosure.

While the best modes for carrying out the disclosure have been described in detail, those familiar with the art to which this disclosure relates will recognize various alternative designs and embodiments lying within the scope of the appended claims. It is intended that the subject matter detailed in the above description and/or shown in the accompanying drawings shall be interpreted as illustrative of the present teachings and non-limiting.

What is claimed is:

1. A test system for detecting driver impairment aboard a motor vehicle having a vehicle interior, the test system comprising:
    a plurality of sensors positioned within the vehicle interior, the sensors including at least a touch screen and a microphone;
    an electronic control unit (ECU) in communication with the sensors, having a processor configured to access a calibrated baseline performance database, and including instructions for performing a cognitive response test, wherein the ECU is configured, in response to receiving a start request indicative of a requested start event of the motor vehicle, to execute the instructions and thereby initiate the cognitive response test via the sensors, determine a test performance of a driver of the motor vehicle during the cognitive response test while the motor vehicle is off, compare the determined test performance to the calibrated baseline performance database to thereby determine a test score, and execute a control action aboard the motor vehicle in response to the test score;

wherein the cognitive response test includes at least two of a reflex response time test in which the ECU is configured to display moving icons on the touch screen, an audible recognition test in which the ECU is configured to broadcast one or more questions within the vehicle interior, and/or an eye-tracking test in which the ECU is configured to direct the driver to look at different areas of the touch screen; and wherein the ECU is configured to randomize an order of performance of the reflex response time test, the audible recognition test, and/or the eye-tracking test.

2. The test system of claim 1, wherein the motor vehicle includes a vehicle telematics unit (VTU) in communication with the ECU, the ECU is configured to periodically update the calibrated baseline performance database using telematics data from the VTU, and the telematics data is descriptive of actual driving behavior of the driver.

3. The test system of claim 2, wherein the actual driving behavior includes a previously demonstrated braking, acceleration, speed, and/or velocity behavior.

4. The test system of claim 1, wherein the ECU is programmed with a Cognitive Response Ignition Disabler (CRID) logic block, and wherein the ECU, via the CRID logic block, is configured to prevent or delay a starting event of the motor vehicle when the test score is a failing test score.

5. The test system of claim 1, wherein the ECU is configured to simultaneously detect touch events in which the driver touches the moving icons of the reflex response time test.

6. The test system of claim 1, wherein the ECU is configured to detect a verbal response of the driver via the microphone of the audible recognition test.

7. The test system of claim 1, wherein the sensors include an eye-tracking camera, and wherein the ECU is configured to detect a response speed of the driver via the eye-tracking camera as the driver looks at the different areas of the eye-tracking test.

8. The test system of claim 1, wherein the control action includes displaying alternative ride options via the touch screen when the test score is a failing test score.

9. The test system of claim 1, further comprising: a memory device of the ECU or accessible by the ECU, and on which is recorded the calibrated baseline performance database.

10. The test system of claim 9, wherein the calibrated baseline performance database includes multiple data clusters, the ECU is configured to assign the driver to one of the data clusters as an assigned cluster, and to thereafter compare the test score to the assigned cluster to detect a threshold variance from the assigned cluster and thereby determine when the test score is a failing test score.

11. A method for detecting driver impairment aboard a motor vehicle having a vehicle interior, the method comprising:

receiving a start request indicative of a requested start event of the motor vehicle;

determining, via an electronic control unit (ECU), a performance of a driver of the motor vehicle from a battery of cognitive response tests performed using a plurality of onboard sensors while the motor vehicle is in an off state, the onboard sensors including at least a touch screen and a microphone, and the cognitive response tests include at least two of a reflex response time test in which the ECU is configured to display moving icons on the touch screen, an audible recognition test in which the ECU is configured to broadcast one or more questions within the vehicle interior, and/or an eye-tracking test in which the ECU is configured to direct the driver to look at different areas of the touch screen;

randomizing a selection of the at least two of the reflex response time test, the audible recognition test, and/or the eye-tracking test via the ECU;

comparing the performance of the driver to a calibrated baseline performance using the ECU to thereby determine a test score; and executing a control action aboard the motor vehicle, via the ECU, in response to the test score.

12. The method of claim 11, wherein the motor vehicle includes a vehicle telematics unit (VTU) in communication with the ECU, the method further comprising:

periodically updating the calibrated baseline performance via the ECU using telematics data from the VTU that is descriptive of actual driving behavior of the driver.

13. The method of claim 12, wherein the actual driving behavior includes a previously demonstrated braking, acceleration, speed, and/or velocity.

14. The method of claim 11, further comprising: using a Cognitive Response Ignition Disabler (CRID) logic block of the ECU to prevent or delay a starting event of the motor vehicle when the test score is a failing test score.

15. The method of claim 11, wherein determining the performance of the driver of the motor vehicle to the battery of the cognitive response tests includes determining the reflex response time test, via the ECU, by displaying the moving icons on the touch screen, and by simultaneously detecting touch events in which the driver touches the moving icons.

16. The method of claim 11, wherein determining the performance of the driver of the motor vehicle to the battery of the cognitive response tests includes determining the audible recognition test by broadcasting the one or more questions within the vehicle interior, and then detecting a verbal response of the driver via the microphone.

17. The method of claim 11, wherein the onboard sensors include an eye-tracking camera, and wherein determining the performance of the driver of the motor vehicle to the battery of the cognitive response tests includes determining the eye-tracking test by directing the driver to look at the different areas of the touch screen, via the ECU, and thereafter detecting a response speed of the driver via the eye-tracking camera as the driver looks at the different areas.

18. The method of claim 11, wherein the control action includes displaying alternative ride options via the touch screen when the test score is a failing test score.

19. A motor vehicle comprising:
a body defining a vehicle interior;
a set of road wheels connected to the body; and
a test system for detecting driver impairment aboard the motor vehicle, including:
a plurality of sensors positioned within the vehicle interior, the sensors including a touch screen, a microphone, and an eye-tracking camera; and
an electronic control unit (ECU) in communication with the sensors, having a processor configured to access a calibrated baseline performance database, and including instructions for performing a cognitive response test, wherein the ECU is configured, in response to receiving a start request indicative of a requested start event of the motor vehicle, to execute the instructions and thereby initiate the cognitive response test using the sensors, the cognitive response test including:
- a reflex response time test using the touch screen, and in which the ECU is configured to display moving icons on the touch screen and simultaneously detect touch events in which a driver touches the moving icons;
- an audible recognition test using the microphone, and in which the ECU is configured to broadcast one or more questions within the vehicle interior and detect a verbal response of the driver via the microphone; and
- an eye-tracking test using the eye-tracking camera, and in which the ECU is configured to direct the driver to look at different areas of the touch screen and simultaneously detect a response speed of the driver via the eye-tracking camera;

wherein the ECU is configured to randomize an order of performance of the reflex response time test, the audible recognition test, and the eye-tracking test, and the ECU is configured to determine a test score of the driver of the motor vehicle during the cognitive response test while the motor vehicle is off, compare the test score to the calibrated baseline performance database to detect a failing test result, and execute a control action aboard the motor vehicle in response to the failing test result, including temporarily disabling or immobilizing the motor vehicle.

20. The motor vehicle of claim 19, further comprising a vehicle telematics unit (VTU), wherein the ECU is configured to periodically update the calibrated baseline performance database using telematics data from the VTU that is descriptive of actual driving behavior of the driver including previously-demonstrated braking, acceleration, speed, and/or velocity behavior.

\* \* \* \* \*